US010548928B2

(12) United States Patent
Grompone et al.

(10) Patent No.: US 10,548,928 B2
(45) Date of Patent: Feb. 4, 2020

(54) **USE OF *LACTOBACILLUS PARACASEI* FOR PROMOTING RECOVERY OF THE INTESTINAL MICROBIOTA DIVERSITY AFTER DYSBIOSIS**

(71) Applicants: COMPAGNIE GERVAIS DANONE, Paris (FR); INSTITUT NATIONAL DE LA RECHERCHE AGRONOMIQUE, Paris (FR)

(72) Inventors: Gianfranco Grompone, Paris (FR); Muriel Derrien, Bures sur Yvette (FR); Johan Van Hylckama Vlieg, Chavenay (FR); Pascale Serror, Jouy-en-josas (FR); Lionel Rigottier-Gois, Palaiseau (FR); Laureen Crouzet, Blanzat (FR); Claire Cherbuy, Les Ulis (FR)

(73) Assignees: COMPAGNIE GERVAIS DANONE, Paris (FR); INSTITUT NATIONAL DE LA RECHERCHE AGRNOMIQUE, Paris (FR)

( * ) Notice: Subject to any disclaimer, the term of this patent is extended or adjusted under 35 U.S.C. 154(b) by 0 days.

(21) Appl. No.: 15/303,418

(22) PCT Filed: Apr. 15, 2015

(86) PCT No.: PCT/IB2015/052752
§ 371 (c)(1),
(2) Date: Oct. 11, 2016

(87) PCT Pub. No.: WO2015/159240
PCT Pub. Date: Oct. 22, 2015

(65) Prior Publication Data
US 2017/0028001 A1 Feb. 2, 2017

(30) Foreign Application Priority Data
Apr. 15, 2014 (WO) .................. PCT/IB2014/060741

(51) Int. Cl.
*A61K 35/747* (2015.01)
*A23L 33/135* (2016.01)
*C12R 1/225* (2006.01)
*A23C 9/123* (2006.01)

(52) U.S. Cl.
CPC .......... *A61K 35/747* (2013.01); *A23C 9/1234* (2013.01); *A23L 33/135* (2016.08); *C12R 1/225* (2013.01); *A23V 2002/00* (2013.01); *A23Y 2220/63* (2013.01)

(58) Field of Classification Search
CPC ...... C12R 1/225; A61K 35/747; A23L 33/135
See application file for complete search history.

(56) References Cited

U.S. PATENT DOCUMENTS

| 8,557,561 B2 * | 10/2013 | Chambaud | A23C 9/1234 424/93.45 |
| 2013/0202738 A1 * | 8/2013 | Daval | A23C 9/1234 426/43 |

FOREIGN PATENT DOCUMENTS

| EP | 2 348 102 A1 | 7/2011 | |
| EP | 2348102 A1 * | 7/2011 | ........... A61K 35/747 |
| WO | 2007/140621 A1 | 12/2007 | |
| WO | 2009/130423 A2 | 10/2009 | |
| WO | 2013/079994 A1 | 6/2013 | |
| WO | WO 2013/079994 * | 6/2013 | |

OTHER PUBLICATIONS

Lenoir-Wijnkoop et al., Frontiers in Pharmacology, Feb. 2014, vol. 5, Article 13, p. 1-9.*
Arias, C.A., and B.E. Murray, "The Rise of the Enterococcus: Beyond Vancomycin Resistance," Nature Reviews: Microbiology 10(4):266-278, Apr. 2012.
Collins, S.M., and P. Bercik, "The Relationship Between Intestinal Microbiota and the Central Nervous System in Normal Gastrointestinal Function and Disease," Gastroenterology 136(6):2003-2014, May 2009.
Holzapfel, W.H., and U. Schillinger, "Introduction to Pre- and Probiotics," Food Research International 35(2-3):109-116, Jan. 2002.
International Search Report and Written Opinion dated Aug. 20, 2015, issued in corresponding International Application No. PCT/IB2015/052752, filed Apr. 15, 2015, 10 pages.
Kang, S., et al., "Dysbiosis of Fecal Microbiota in Crohn's Disease Patients as Revealed by a Custom Phylogenetic Microarray," Inflammatory Bowel Disease 16(12):2034-2042, Dec. 2010.
Schlee, M., et al., "Probiotic Lactobacilli and VSL#3 Induce Enterocyte β-Defensin 2," Clinical and Experimental Immunology 151(3):528-535, Mar. 2008.
Vidal, M., et al., "Probiotics and Intestinal Colonization by Vancomycin-Resistant Enterococci in Mice and Humans," Journal of Clinical Microbiology 48(7):2595-2598, Jul. 2010.

* cited by examiner

*Primary Examiner* — Ruth A Davis
(74) *Attorney, Agent, or Firm* — Christensen O'Connor Johnson Kindness PLLC

(57) ABSTRACT

The present invention provides the use of *Lactobacillus paracasei*, for maintaining or increasing the intestinal microbiota diversity in a subject having dysbiosis.

6 Claims, 6 Drawing Sheets

USE OF *LACTOBACILLUS PARACASEI* FOR PROMOTING RECOVERY OF THE INTESTINAL MICROBIOTA DIVERSITY AFTER DYSBIOSIS

FIELD OF THE INVENTION

The present invention relates to the field of probiotics. In particular, the invention pertains to the use of *Lactobacillus paracasei* (*L. paracasei*) for the recovery of intestinal microbiota diversity in a subject. In a particular embodiment, the present invention concerns the use of *Lactobacillus paracasei* subsp. *paracasei*, for accelerating the decrease of *Enterococcus faecalis* in the intestinal microbiota of a subject having an intestinal dysbiosis.

BACKGROUND

According to a definition approved by a joint Food and Agriculture Organization of the United Nations/World Health Organization (FAO/WHO) expert Consultation on Health and Nutritional properties of powder milk with live lactic acid bacteria in 2001, probiotics are "live microorganisms which when administered in adequate amounts confer a health benefit on the host". Probiotic bacteria have been described among species belonging to the genera *Lactobacillus, Bifidobacterium, Streptococcus* and *Lactococcus*, which are commonly used in the dairy industry. Probiotics are thought to intervene at the level of the gut microbiota by impeding the development of pathogenic microorganisms and/or by acting more directly on the immune system.

Opportunistic bacterial infections responsible for healthcare associated infections (HAIs) contribute significantly to patient mortality and morbidity, as well as healthcare costs both in developed and developing countries (WHO, 2008). The gastrointestinal tract (GIT) is a reservoir for opportunistic pathogens, which benefit from the disruption of the intestinal microbiota balance, or dysbiosis, to invade and infect susceptible patients. Antibiotic treatments have deleterious effects on the diversity of the intestinal microbiota and they promote expansion of bacterial human opportunistic pathogens including *Enterococcus faecalis, Enterococcus faecium* or *Clostridium difficile*.

Having acquired antibiotic resistance and other pathogenic traits, multi-drug resistant colonizing and/or invasive *E. faecalis* isolates, which cause serious nosocomial infections, are grouped in seven hospital-adapted complexes designated as High-Risk Enterococcal Clonal Complexes (HiRECCs). Proliferation and persistence of HiRECCs within the GIT are a major risk of developing a vancomycin-resistant enterococcal (VRE) infection, highlighting a need for a better understanding of the biological and biochemical factors involved in colonization of the GIT by *E. faecalis*. Isolates belonging to HiRECC-2 are among the most common causes of *E. faecalis* infections in the United States and in several European countries. Some *E. faecalis* strains acquired pathogenic traits and can cause severe infections. Indeed, they can colonize the GIT and/or cross the intestinal epithelial barrier and enter the bloodstream. Futhermore, *Enterococcus* spp. contribute to community-acquired intra-abdominal infections and count among the ten most frequently isolated micro-organisms in healthcare-associated infections (HCAI). Hence, reducing the proliferation and persistence of *E. faecalis*, especially of HiRECCs in the GIT reduces the risk of developing not only a GIT infection, but also an intra-abdominal infection.

It is clear from the above that there is a need for alternatives or complements to antibiotics for the treatment or for the prevention of *E. faecalis* infection.

The "gut microbiota" designates the population of microorganisms living in the intestine of any organism belonging to the animal kingdom (human, animal, insect, etc.). While each individual has a unique microbiota composition (60 to 80 bacterial species are shared by more than 50% of a sampled population of a total of 400-500 different bacterial species/individual), it always fulfils similar main physiological functions and has a direct impact on the individual's health:

- it contributes to the digestion of certain foods that the stomach and small intestine are not able to digest (mainly non-digestible fibers);
- it contributes to the production of some vitamins (B and K);
- it protects against aggressions from other microorganisms, maintaining the integrity of the intestinal mucosa;
- it plays an important role in the development of a proper immune system;
- a healthy, diverse and balanced gut microbiota is key to ensuring proper intestinal functioning.

Taking into account the major role that gut microbiota plays in the normal functioning of the body and the different functions it accomplishes, it is sometimes considered to be an "organ". However, it is an "acquired" organ, as babies are born sterile; that is, intestine colonization starts at birth and evolves afterwards.

The magnitude of disturbance of the gut microbiota following a perturbation such as a dietary change, an antibiotic treatment and an invasion by an exogenous microbe, and the speed and extent of the recovery to the pre-perturbation state, was defined as "the resilience of the microbiota". Resilience of the microbiota varies across individuals and between different perturbations within an individual.

From the above, it appears that there is also an important need for treatments for increasing the resilience of the microbiota.

Growing evidence shows that probiotics or fecal microbiota transplantation prevent or treat a number of diseases, including intestinal infections. Such approaches were also associated with higher clearance of intestinal VRE in mice.

Surprisingly the inventors have found that the bacterial species *Lactobacillus paracasei* is capable of promoting recovery of intestinal microbiota diversity and/or decreasing the load of *E. faecalis* strains in vivo.

Accordingly, a subject of the present invention is the use of *Lactobacillus paracasei*, for increasing the resilience of the gut microbiota. In particular, the present invention pertains to the use of *Lactobacillus paracasei*, for the increase of intestinal microbiota diversity of a subject. In a specific embodiment, the present invention consists in the use of a *Lactobacillus paracasei* strain for accelerating the decrease of *Enterococcus faecalis* in the intestinal microbiota of a subject having an intestinal dysbiosis caused by antibiotics.

Further aspects of the present invention provide the use of *Lactobacillus paracasei* in the prevention, reduction or treatment of intestinal dysbiosis; and/or prevention of a disease caused by a pathogen present in the gastrointestinal tract; and/or increase in the level of short-chain fatty acid in a subject.

The invention also provides compositions comprising *Lactobacillus paracasei* for use according to the present invention.

DETAILED DESCRIPTION

In the present text, the phrases "maintain the microbiota diversity" will be used to express that species diversity (species richness and/or species evenness) of the microbiota of an individual will not be significantly modified or affected, especially in case of dysbiosis. In particular, maintaining the microbiota diversity could help the subject to recover faster in case of risk of dysbiosis or could avoid the dysbiosis to worse. The phrases "increase of microbiota diversity", "promote recovery of microbiota diversity", "treatment/decrease/reduction/of dysbiosis" etc. will be used to express an increase in species diversity (species richness and/or species evenness) of the microbiota of an individual. Methods for the calculation of species diversity, species richness and species evenness are known in the art and include but are not limited to Simpson's Index, Simpson's Index of Diversity and Simpson's Reciprocal Index, Chao Index and Shannon Index.

In addition, "accelerate the increase of the intestinal microbiota diversity", "promote recovery of the intestinal microbiota diversity", "favour the return to a baseline/normal/healthy intestinal microbiota diversity", "accelerate the decrease/reduction/disappearance of the dysbiosis" etc. will be used to express that the diversity (richness and/or evenness) of the microbiota of individuals having an intestinal dysbiosis after a treatment by antibiotics increases statistically more rapidly in subjects who take the probiotic strain than in control subjects who do not, so that the structure of the microbiota three weeks after the antibiotic treatment is statistically closer to the structure before said treatment in subjects who take the probiotic strain than in control subjects who do not. As used herein the term "dysbiosis" shall be taken to mean a change in microbiota commensal species diversity as compared to a healthy or general population and shall include decrease of beneficial microorganisms and/or increase of pathobionts (pathogenic or potentially pathogenic microorganisms) and/or decrease of overall microbiota species diversity. Many factors can harm the beneficial members of the intestinal microbiota leading to dysbiosis, including antibiotic use, psychological and physical stress, radiation, and dietary changes. Antibiotic use is the most common and significant cause of major alterations in normal microbiota. Thus, as used herein, the term "antibiotic-induced dysbiosis"refers to dysbiosis caused by antibiotic comprising the promotion of overgrowth of bacterial opportunistic pathogens including *Enterococcus faecalis, Enterococcus faecium* or *Clostridium difficile*. As used herein the term "dairy composition" shall be taken to mean a milk-based composition suitable for animal consumption, in particular human consumption.

As used herein the term "milk" shall be taken to include vegetal or animal milk, such as but not limited to soya, almond, spelt, oat, hemp, coconut, rice, goat, ewe, or cow milk.

As used herein the term "x % (w/w)" is considered equivalent to "x g per 100 g".

As used herein reference to a bacterial strain or species shall be taken to include bacteria derived therefrom wherein said bacteria retain the capacity to decrease intestinal dysbiosis of a subject, preferably a subject having an antibiotic-induced dysbiosis. To assess this capacity, the same model as described in the Examples below can be used. Strains derived from a parent strain which can be used according to the present invention include mutant strains and genetically transfouned strains. These mutants or genetically transformed strains can be strains wherein one or more endogenous gene(s) of the parent strain has (have) been mutated, for instance to modify some of their metabolic properties (e.g., their ability to ferment sugars, their resistance to acidity, their survival to transport in the gastrointestinal tract, their post-acidification properties or their metabolite production). They can also be strains resulting from the genetic transformation of the parent strain to add one or more gene(s) of interest, for instance in order to give to said genetically transformed strains additional physiological features, or to allow them to express proteins of therapeutic or vaccinal interest that one wishes to administer through said strains. These mutants or genetically transformed strains can be obtained from the parent strain by means of conventional techniques for random or site-directed mutagenesis and genetic transformation of bacteria, or by means of the technique known as "genome shuffling". In the present text, strains, mutants and variants derived from a parent species or strain and retaining the ability to maintain or increase intestinal microbiota diversity of a subject having an antibiotics-induced dysbiosis will be considered as being encompassed by reference to said parent species or strain, e.g. the phrases "*Lactobacillus paracasei*" and "strain CNCM I-3689" shall be taken to include strains, mutants and variants derived therefrom.

As used herein the term "food supplement" shall be taken to mean a product made from compounds usually used in foodstuffs, but which is in the form of tablets, powder, capsules, potion or any other form usually not associated with aliments, and which has beneficial effects for one's health.

As used herein the term "functional food" shall be taken to mean an aliment which has beneficial effects for one's health in addition to providing nutrients. In particular, food supplements and functional food can have a physiological effect—for the prophylaxis, amelioration or treatment of a disease, for example a chronic disease.

As used herein the term "fermented dairy" or "fermented milk" refers to a composition derived from a dairy or milk composition respectively by the acidifying action of at least one lactic acid bacterium, which may be comprised in a ferment, a culture or a starter.

As used herein the term "spoonable" shall be taken to mean a solid or semi-solid that may be consumed by means of a spoon or other utensil.

As used herein the phrases "accelerate the decrease of *E. faecalis*", "decrease the load of *E. faecalis*", "promote the decrease of *E. faecalis*", etc. will be used to express that the amount of *E. faecalis* present in the microbiota of individuals having an intestinal dysbiosis after a treatment by antibiotics decreases more rapidly in subjects who take the probiotic strain than in control subjects who do not.

Uses of *Lactobacillus Paracasei*

The present invention provides the use of *L. paracasei*, preferably subspecies *paracasei*, further preferably strain CNCM I-3689, for use to maintain or increase the intestinal microbiota diversity in a subject, preferably a subject having intestinal dysbiosis.

Accordingly, in one embodiment the present invention provides the use of *L. paracasei*, preferably subspecies paracasei, further preferably strain CNCM I-3689, for the prevention or decrease of intestinal dysbiosis in a subject. *L. paracasei* subsp. *paracasei* strain CNCM I-3689 was deposited, according to the Budapest Treaty, at CNCM (Collection Nationale de Cultures de Microorganismes, 25 rue du Docteur Roux, Paris) on Nov. 9, 2006. This strain is disclosed in International Patent Application WO 2009/130423.

In a preferred embodiment the intestinal dysbiosis is caused by or subsequent to antibiotic treatment of the subject. Antibiotic associated dysbiosis may typically becharacterized by an increase in gastrointestinal *Enterococcus faecalis, Enterococcus faeciwn* and/or *Clostridium difficile*.

Surprisingly the inventors have found that *L. paracasei* not only promotes intestinal microbiota diversity in a subject but also reduces the gastrointestinal opportunistic pathogen *Enterococcus faecalis*. Accordingly, the present invention provides the use of *L. paracasei*, preferably subspecies *paracasei*, further preferably strain CNCM I-3689, for the reduction or accelerating the decrease of *Enterococcus faecalis*. In an alternative embodiment, the present invention provides the use of *L. paracasei*, preferably subspecies *paracasei*, further preferably strain CNCM I-3689, for preventing translocation of *Enterococcus faecalis* across the intestinal barrier and/or for preventing intra-abdominal infection by *Enterococcus faecalis*. In a further embodiment the present invention provides the use of *L. paracasei*, preferably subspecies *paracasei*, further preferably strain CNCM I-3689, for the reduction or accelerating the decrease of drug resistant enterococci, preferably of HiRECCs subsequent to antibiotic treatment. Accordingly in one embodiment the invention provides the use of *L. paracasei*, preferably subspecies *paracasei*, further preferably strain CNCM I-3689, for the reduction or accelerating the decrease of antibiotic-resistant *E. faecalis*, typically intestinal. Typically said are resistant to one or more antibiotics selected from penicillins, cephalosporins, fluoroquinolones, aminoglycosides and glycopeptides.

Preferably the subject has intestinal dysbiosis. In a preferred embodiment, the intestinal dysbiosis is caused by or subsequent to antibiotic treatment of the subject. Preferably the *Enterococcus faecalis* is gastrointestinal, more preferably, intestinal.

Compositions

A further aspect of the present invention provides compositions comprising *L. paracasei*, preferably subspecies *paracasei*, further preferably strain CNCM I-3689, for uses according to the present invention.

Accordingly, in a preferred embodiment of the present invention, the strain *L. paracasei*, preferably subspecies *paracasei*, further preferably strain CNCM I-3689, is provided as an orally administrable composition. In such a composition, said strain can be used in the form of whole bacteria which may be living or dead. Alternatively, said strain can be used in the form of a bacterial lysate. Preferably, the bacterial cells are present as living and viable cells.

According to the present invention, the composition can be in any form suitable for oral administration. This includes for instance solids, semi-solids, liquids, and powders. Semi-solid compositions, such as yogurts, and liquid compositions, such as drinks, are preferred.

The composition preferably comprises at least $1.10^6$ colony forming units (cfu), at least $1.10^7$ colony forming units (cfu) or preferably at least $1.10^8$ cfu per gram weight, of *L. paracasei*, preferably subspecies *paracasei*, preferably the strain CNCM I-3689. Preferably also the composition according to the invention comprises up to about $10^{11}$, more preferably at least $10^{10}$ and most preferably at least $10^9$ colony forming unit (CFU) of *L. paracasei*, preferably subspecies *paracasei*, preferably the strain CNCM I-3689, according to the invention per gram (g) of composition according to the invention.

The composition can further comprise other strains of *Lactobacillus* and/or other strains of bacteria than the strains mentioned above, in particular probiotic strain(s), such as *Streptococcus thermophilus, Bifidobacterium* and *Lactococcus* strain(s).

The composition can be a pharmaceutical composition or a nutritional composition. According to a preferred embodiment, the composition is a nutritional composition such as a food product (including a functional food) or a food supplement.

Nutritional compositions which can be used according to the invention include dairy compositions, preferably fermented dairy compositions. The fermented compositions can be in the form of a liquid or in the form of a dry powder obtained by drying the fermented liquid. Examples of dairy compositions include fermented milk and/or fermented whey in set, stirred or drinkable form, cheese and yoghurt. The fermented product can also be a fermented vegetable, such as fermented soy, cereals and/or fruits in set, stirred or drinkable forms. Nutritional compositions which can be used according to the invention also include baby foods, infant milk formulas and infant follow-on formulas. In a preferred embodiment, the fermented product is a fresh product. A fresh product, which has not undergone severe heat treatment steps, has the advantage that the bacterial strains present are in the living form.

It is particularly preferred that the composition according to the invention is a dairy composition, in particular a fermented dairy composition.

Preferably, the dairy composition according to the invention comprises or derives (in particular by fermentation) from a composition containing from 30 to 100% (w/w) milk, more preferably from 50 to 100% (w/w) milk and even more preferably from 70 to 100% (w/w) milk. Preferably also, the dairy composition according to the invention comprises or derives (in particular by fermentation) from a composition essentially consisting of milk or consisting only of milk, preferably to cow milk.

Preferably, the dairy composition according to the invention comprises or derives (in particular by fermentation) from a composition comprising one or both of skimmed or non-skimmed milk. Preferably said milk or milks may be in liquid, powdered and/or concentrated form. In one embodiment said milk or milks may be enriched or fortified with further milk components or other nutrients such as but not limited to vitamins, minerals, trace elements or other micronutrients.

The fermented dairy composition is derived from a dairy composition according to the invention by the acidifying action of at least one lactic acid bacterium, which may be comprised in a ferment, a culture or a starter. More preferably said fermented dairy composition according to the invention is obtained by the acidifying action of at least one, two, three, four, five, six, seven or more lactic acid bacteria strains. Accordingly the "fermented dairy composition" comprises at least one, two, three, four, five, six, seven or more lactic acid bacteria strains.

Methods for the preparation of fermented milk products, such as yogurts or equivalents thereof, are well-known in the art. Typically a fermented milk product is prepared by culture of heat-treated (e.g. pasteurized) skimmed and/or non-skimmed milks with suitable microorganisms to provide a reduction in pH. The selection of suitable microorganisms (e.g. thermophilic lactic acid bacteria) is within the scope of the skilled person.

The dairy composition, in particular the feunented dairy composition, according to the invention, may optionally further comprise secondary ingredients such as fruits, vegetables, nutritive and non-nutritive sweeteners, cereals, flavours, starch, thickeners, preservatives or stabilizers. Preferably the dairy composition, in particular the fermented dairy composition, according to the invention shall comprise up to about 30% (w/w) of said secondary ingredients, e.g. up to about 10%, 15%, 20%, 25% (w/w).

Preferably the dairy composition according to the invention is a fermented dairy composition, more preferably a fermented milk composition that comprises, comprises essentially of or consists of milk that has been subjected to heat treatment at least equivalent to pasteurization, preferably said heat treatment is carried out prior to the preparation of the dairy composition or fermented dairy composition.

Preferably the dairy composition according to the invention is a fermented dairy composition, more preferably a fermented milk composition that comprises above about 0.3 g per 100 g by weight free lactic acid, more preferably the invention provides a fermented milk composition comprising above about 0.7 g or 0.6 g per 100 g by weight free lactic acid.

Preferably the dairy composition according to the invention is a fermented dairy composition, more preferably a fermented milk composition that comprises a protein content at least equivalent to that of the milk or milks from which it is derived.

Preferably the dairy composition according to the invention is a fermented dairy composition, more preferably a fermented milk composition that has a pH equal to or lower than 5, more preferably between about 3.5 and about 4.5.

Preferably the dairy composition according to the invention is a fermented dairy composition, more preferably a fermented milk composition that has a viscosity lower than 200 mPa·s, more preferably lower than 100 mPa·s and most preferably lower that 60 mPa·s, at 10° C., at a shear rate of 64 s-1. In one embodiment the dairy composition according to the invention is a drinkable fermented dairy composition, more preferably a drink fermented milk drink such as but not limited to a yogurt drink, kefir etc. In an alternative embodiment the dairy composition according to the invention is a fermented dairy composition, more preferably a feiniented milk composition that is spoonable. Preferably also, the dairy composition, in particular the fermented dairy composition, according to the invention, or the product according to the invention, may be stored at a temperature of from 1° C. to 10° C.

A single serving portion of the dairy composition, in particular the fermented dairy composition according to the invention, more preferably a fermented milk composition or the product according to the invention is preferably about 50 g, 60 g, 70 g, 75 g, 80 g, 85 g, 90 g, 95 g, 100 g, 105 g, 110 g, 115 g, 120 g, 125 g, 130 g, 135 g, 140 g, 145 g, 150 g, 200 g, 300 g or 320 g or alternatively about 1 oz, 2 oz, 3 oz, 4 oz, 5 oz, 6 oz or 12 oz by weight.

Preferably, the dairy composition, in particular the fermented dairy composition according to the invention, more preferably a fermented milk composition according to the invention comprises at least $10^6$, more preferably at least $10^7$ and most preferably at least $10^8$ colony forming unit (CFU) of *L. paracasei*, preferably subspecies *paracasei*, preferably the strain CNCM I-3689, according to the invention per gram (g) of composition according to the invention.

Therapeutic Uses

A subject of the present invention is also the use of *L. paracasei*, preferably subspecies *paracasei*, preferably the strain CNCM I-3689, or a composition as defined above, for the manufacture of a medicament for the maintaining or increase of intestinal microbiota diversity; and/or prevention or treatment of intestinal dysbiosis. The present invention provides the use of *L.paracasei*, preferably subspecies *paracasei*, further preferably strain CNCM I-3689, for the manufacture of a medicament for the reduction or reduction or accelerating the decrease of *Enterococcus faecalis*. In an alternative embodiment the present invention provides the use of *L. paracasei*, preferably subspecies *paracasei*, further preferably strain CNCM I-3689o, for the manufacture of a medicament for preventing translocation of *Enterococcus faecalis* across the intestinal barrier and/or for preventing intra-abdominal infection by *Enterococcus faecalis*. In a further embodiment the present invention provides the use of *L. paracasei*, preferably subspecies *paracasei*, further preferably strain CNCM I-3689, for the manufacture of a medicament for the reduction or accelerating the decrease of drug resistant enterococci, preferably of HiRECCs subsequent to antibiotic treatment. Accordingly in one embodiment the invention provides the use of *L. paracasei*, preferably subspecies *paracasei*, further preferably strain CNCM I-3689, for the manufacture of a medicament for the reduction or accelerating the decrease of antibiotic-resistant *E. faecalis*, typically intestinal. Typically said *E. faecalis* are resistant to one or more antibiotics selected from penicillins, cephalosporins, fluoroquinolones, aminoglycosides and glycopeptides.

A subject of the present invention is also the use of *L. paracasei*, preferably subspecies paracasei, preferably the strain CNCM I-3689, or a composition as defined above, for the prevention or treatment of intestinal dysbiosis.

The present invention provides the use of *L. paracasei*, preferably subspecies *paracasei*, further preferably strain CNCM I-3689 or, for the treatment of *Enterococcus faecalis* infection. In an alternative embodiment the present invention provides the use of *L. paracasei*, preferably subspecies *paracasei*, further preferably strain CNCM I-3689, for the treatment or prevention of translocation of *Enterococcus faecalis* across the intestinal barrier and/or for treatment or prevention of intra-abdominal infection by *Enterococcus faecalis*. In a further embodiment the present invention provides the use of *L. paracasei*, preferably subspecies *paracasei*, further preferably strain CNCM I-3689, for the treatment of drug resistant enterococci, preferably of HiRECCs subsequent to antibiotic treatment. Accordingly, in one embodiment, the invention provides the use of *L. paracasei*, preferably subspecies *paracasei*, further preferably strain CNCM I-3689, for the treatment of antibiotic-resistant *E. faecalis*, typically intestinal. Typically, said *E. faecalis* are resistant to one or more antibiotics selected from penicillins, cephalosporins, fluoroquinolones, aminoglycosides and glycopeptides.

A subject of the present invention is also a method for the maintaining or increase of intestinal microbiota diversity; and/or prevention or treatment of intestinal dysbiosis said method comprising administering to said subject a therapeutically effective amount of *L. paracasei*, preferably subspecies *paracasei* as defined above, preferably the strain CNCM I-3689, or a composition as defined above.

Determination of a therapeutically effective amount is well known by the person skilled in the art, especially in view of the detailed disclosure provided herein.

A subject of the present invention is also a method for the manufacture of a medicament for the maintaining or increase of intestinal microbiota diversity; and/or prevention or treatment of intestinal dysbiosis comprising incorporating a *L. paracasei*, preferably subspecies paracasei, further preferably strain CNCM I-3689, into at least one pharmaceutically acceptable diluent, carrier or excipient. The present invention provides a method for the manufacture of a medicament for the reduction or accelerating the decrease of *Enterococcus faecalis* comprising incorporating a *L. paracasei*, preferably subspecies *paracasei*, further preferably strain CNCM I-3689, into at least one pharmaceutically acceptable diluent, carrier or excipient. In an alternative embodiment the present invention provides the a method for the manufacture of a medicament for preventing translocation of *Enterococcus faecalis* across the intestinal barrier and/or for preventing intra-abdominal infection by *Enterococcus faecalis* comprising incorporating a *L. paracasei*, preferably subspecies *paracasei*, further preferably strain CNCM I-3689, into at least one pharmaceutically acceptable diluent, carrier or excipient. In a further embodiment the present invention provides a method for the manufacture of a medicament for the reduction or accelerating the decrease of drug resistant enterococci, preferably of HiRECCs subsequent to antibiotic treatmentcomprising incorporating a *L. paracasei*, preferably subspecies *paracasei*, further preferably strain CNCM I-3689, into at least one pharmaceutically acceptable diluent, carrier or excipient. Accordingly in one embodiment the invention provides a method for the manufacture of a medicament for the reduction or accelerating the decrease of antibiotic-resistant *E. faecalis*, typically intestinal comprising incorporating a *L. paracasei*, preferably subspecies *paracasei*, further preferably strain CNCM I-3689, into one pharmaceutically acceptable diluent, carrier or excipient. Typically said *E. faecalis* are resistant to one or more antibiotics selected from penicillins, cephalosporins, fluoroquinolones, aminoglycosides and glycopeptides.

Preferably said subject of the above-described medicaments, uses and/or methods has intestinal dysbiosis, it is further preferred that said dysbiosis is caused by or subsequent to antibiotic treatment of the subject. Preferably the *Enterococcus faecalis* of the above-described medicaments, uses and/or methods is gastrointestinal, more preferably, intestinal.

Dosage

In one embodiment the present invention provides the consumption or administration of a dose of between about $10^8$ and about $10^{11}$ colony forming unit (CFU) of *L. paracasei*, preferably subspecies *paracasei*, further preferably strain CNCM I-3689; preferably between about $10^8$ and about $10^9$, more preferably between about $10^9$ and about $10^{10}$ colony forming unit (CFU) and in an alternative embodiment between about $10^{10}$ and about $10^{11}$ colony forming unit (CFU) of *L. paracasei*, preferably subspecies *paracasei*, further preferably strain CNCM I-3689 for the uses and methods as disclosed herein. In a further embodiment at least 1, 2, 3, or 4 doses are provided within a 24 hour time period. It is further preferred that the daily dosage regimen is maintained for at least about 1, 2, 3, 4, 5, 6 or 7 days, or in alternative embodiment for at least about 1, 2, 3, 4, 5, 6 or 7 weeks.

Accordingly, in one embodiment the present invention provides the daily consumption or administration of at least 1, 2, 3, or 4 servings of the dairy composition, in particular the fermented dairy composition according to the invention, more preferably a fermented milk composition according to the invention. Each serving may be consumed or administered individually, or a plurality of servings may be consumed or administered in a single instance. Each of said servings may be consumed at mealtimes or between mealtimes (e.g. as a snack, subsequent to sporting activities etc. . . . ).

A single serving portion of the dairy composition, in particular the fermented dairy composition according to the invention, more preferably a fermented milk composition, according to the invention is preferably about 50 g, 60 g, 70 g, 75 g, 80 g, 85 g, 90 g, 95 g, 100 g, 105 g, 110 g, 115 g, 120 g, 125 g, 130 g, 135 g, 140 g, 145 g, 150 g, 200 g, 300 g or 320 g or about 1 oz, 2 oz, 3 oz, 4 oz, 5 oz, 6 oz or 12 oz by weight.

Preferably, the composition according to the invention comprises at least $10^6$, more preferably at least $10^7$ and most preferably at least $10^8$ colony forming unit (CFU) of *L. paracasei*, preferably subspecies *paracasei*, further preferably strain CNCM I-3689, according to the invention per gram (g) of composition according to the invention. Preferably also the composition according to the invention comprises the at least $10^{11}$, more preferably at least $10^{10}$ and most preferably at least $10^9$ colony forming unit (CFU) of *L. paracasei*, preferably subspecies *paracasei*, more preferably strain CNCM I-3689, bacteria per gram (g) of composition according to the invention.

For example, in one embodiment the present invention provides the daily consumption of at least 2 or at least 3 servings of a 100 g or 125 g portion of a fermented milk product comprising between about at least $10^7$ and at least $10^8$ colony forming units (CFU) *L. paracasei*, preferably subspecies *paracasei*, more preferably strain I-3689 or per g product. In a further embodiment said daily level of consumption is maintained over a period of at least 1, 2, 3, 4 or more weeks.

The present invention will be understood more clearly from the further description which follows, which refers to examples illustrating the capacity of the *L. paracasei* of decreasing dysbiosis in vivo.

BRIEF DESCRIPTION OF THE FIGURES

FIG. 3 shows the relative abundance of the Actinobacteria, Bacteroidetes, Filinicutes & Proteobacteria phylum at Day 0 ("baseline"

EXAMPLES

Methods

Bacterial Growth

Figure 1:
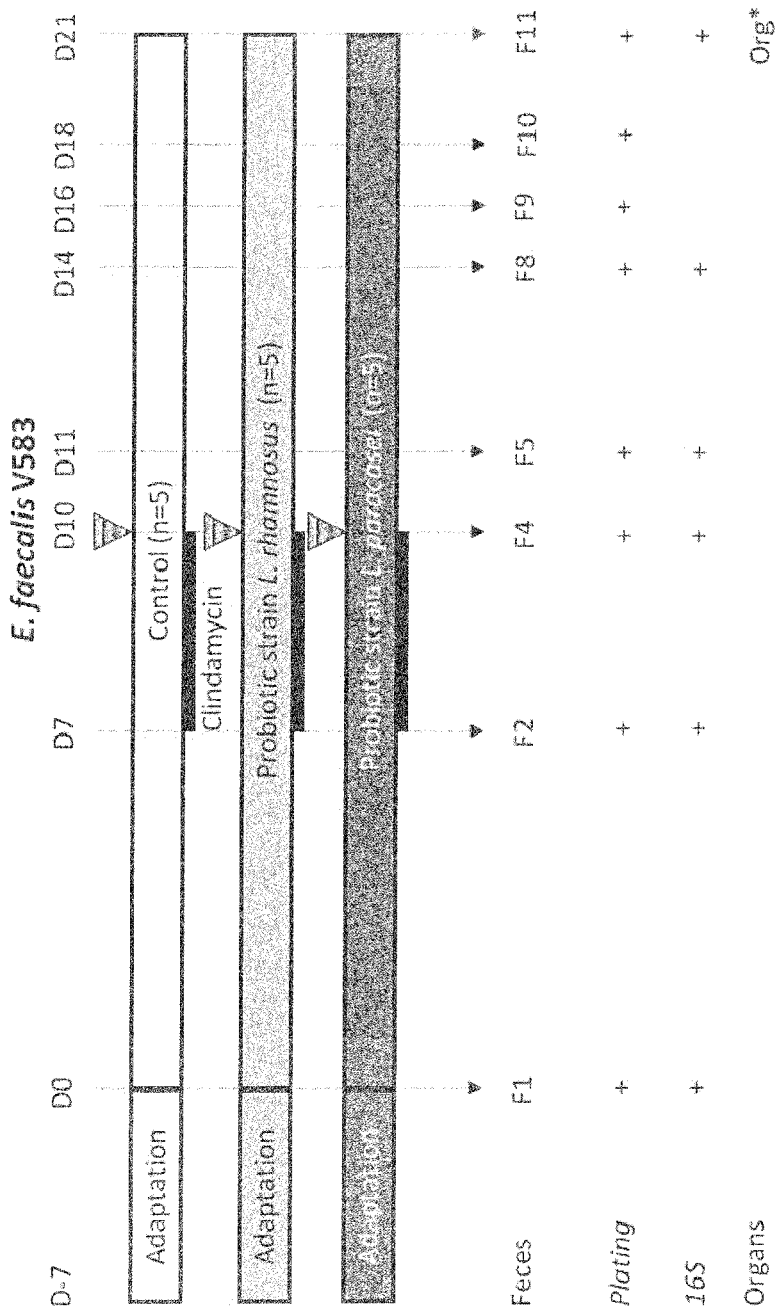
FIG. 1 is a scheme representing the sequence of the experiments.

*E. faecalis* V583 strain was grown in M17 supplemented with 0.5% glucose (GM17) and collected by centrifugation 1 h after reaching stationary phase. Bacterial cells were washed twice with 0.9% saline solution and stored as a dry frozen pellet at −80° C. This strain belongs to CC2 and was the first vancomycin resistant isolate reported in the United States (Sahm et al., 1989).

Probiotic strains were grown in MRS media, and collected as describe above.

At least two days before inoculation, the frozen bacteria were suspended in a saline solution and serial dilutions were plated on GM17 or MRS agar plates to determine the bacterial count of the pellet.

Mouse *E. faecalis* Model Colonization

Mouse experiments were performed using specific pathogen-free male CF-1 mice (Harlan, USA), 6-8-weeks. A total of 5 mice were housed in each cage and were fed with autoclaved food and water ad libitum.

They received a daily dose of $10^9$ CFU of probiotic strain in 0.1 ml of 0.9% saline solution by orogastric inoculation using a steel feeding tube (Ecimed). *Lactobacillus rhamnosus* CNCM I-3690 was administered to the Lr group and *Lactobacillus paracasei* CNCM I-3689 for the Lp group. Animals from the control group received 0.1 ml of 0.9% saline solution by the same way. After one week of probiotic treatment, a dose of 1.4 mg/day of clindamycin was administered subcutaneously daily for three days. One day later, $10^{10}$ colony-forming units (CFU) of *E. faecalis* (vancomycin-resistant enterococci, noted "VRE") strain V583 in 0.1 ml of 0.9% saline solution were administered by orogastric inoculation using a steel feeding tube (Ecimed).

Statistical Analysis

Differences in bacterial counts were analyzed by the Mann-Whitney test (GraphPad). Differences were considered significant when $P<0.05$.

Microbiota Analysis

Faecal samples were collected at D0 (baseline), and D21 (sacrifice). DNA was extracted using Godon et al procedure (Godon, 1997). For pyrosequencing, V3-V5 region of the 16S rRNA gene was amplified using key-tagged eubacterial primers (Lifesequencing S.L., Valencia, Spain) based on design of Sim et al 2012. PCR reactions were performed with 20 ng of metagenomic DNA, 200 µM of each of the four deoxynucleoside triphosphates, 400 nM of each primer, 2.5 U of FastStart HiFi Polymerase, and the appropriate buffer with $MgCl_2$ supplied by the manufacturer (Roche, Mannheim, Germany), 4% of 20 g/mL BSA (Sigma, Dorset, United Kingdom), and 0.5 M Betaine (Sigma). The inial cycling consisted of initial denaturation at 94° C. for 2 minutes followed by 35 cycles of denaturation at 94° C. for 20 seconds, annealing at 50° C. for 30 seconds, and extension at 72° C. for 5 minutes. Amplicons were combined in a single tube in equimolar concentrations. The pooled amplicon mixture was purified twice (AMPure XP kit, Agencourt, Takeley, United Kingdom) and the cleaned pool requantified using the PicoGreen assay (Quant-iT, PicoGreen DNA assay, Invitrogen). Subsequently, an amplicon submitted to the pyrosequencing services offered by Life Sequencing S.L. (Valencia, Spain) where EmPCR was performed and subsequently, unidirectional pyrosequencing was carried out on a 454 Life Sciences GS FLX+ instrument (Roche) following the Roche Amplicon Lib-L protocol. Bioinformatic analyses were performed using QIIME v.1.6 (Caporaso, 2010). Data were assigned to 50 samples after filtering according to the following quality criteria: size between 500 and 1000 nt, quality above 25 over a 50 base pairs window, no mismatch authorized in primers and barcode sequences, and absence of polymers larger than 6nt. Remaining reads were clustered into Operational Taxonomic Units (OTUs) defined at 97% identity using cd-hit (Li, 2006) and representative sequences for each OTU were aligned and taxonomically assigned using Greengenes v_13_08 database.

Results: Strain *L. paracasei* CNCM I-3689 Promotes Recovery of Microbiota Composition Diversity and Intestinal Clearance of Vancomycin-Resistant *E. faecalis* V583

Using the *E. faecalis* colonization model, the two probiotic strains *L. paracasei* CNCM I-3689 and *L. rhamnosus* CNCM I-3690 were daily orally administered to mice starting 1 week before antibiotic treatment, until two weeks after arrest of antibiotic treatment and inoculation of VRE. Levels of total enterococci population and VRE were monitored by selective plating. Kinetics and levels of enterococci population as well as kinetic of establishment of *E. faecalis* VRE strain were similar between the control and the probiotic-treated mice (A & B). In contrast, clearance of VRE was significantly different for mice treated with strain *L. paracasei* CNCM I-3689 compared to control and *L. rhamnosus* CNCM I-3690-treated mice (B). VRE were not detected in half of the mice receiving *L. paracasei* 11 days after the arrest of the antibiotic treatment corresponding to D21 of the experiment, and VRE level was significantly decreased in the other half compared to control mice (C).

Figure 2:
FIG. 2 shows the kinetics and levels determined by selective plating of total enterococci population in mice fed with a daily dose of 0.1 ml of 0.9% saline solution (control) or fed by $10^9$ CFU of probiotic strain in 0.1 ml of 0.9% saline solution by orogastric inoculation (A); kinetics and levels of establishment of *E. faecalis* V583 strain (B) and levels of *E. faecalis* V583 11 days after the arrest of the antibiotic treatment corresponding to D21 (C). Experiments were done in triplicate.
Figure 2:
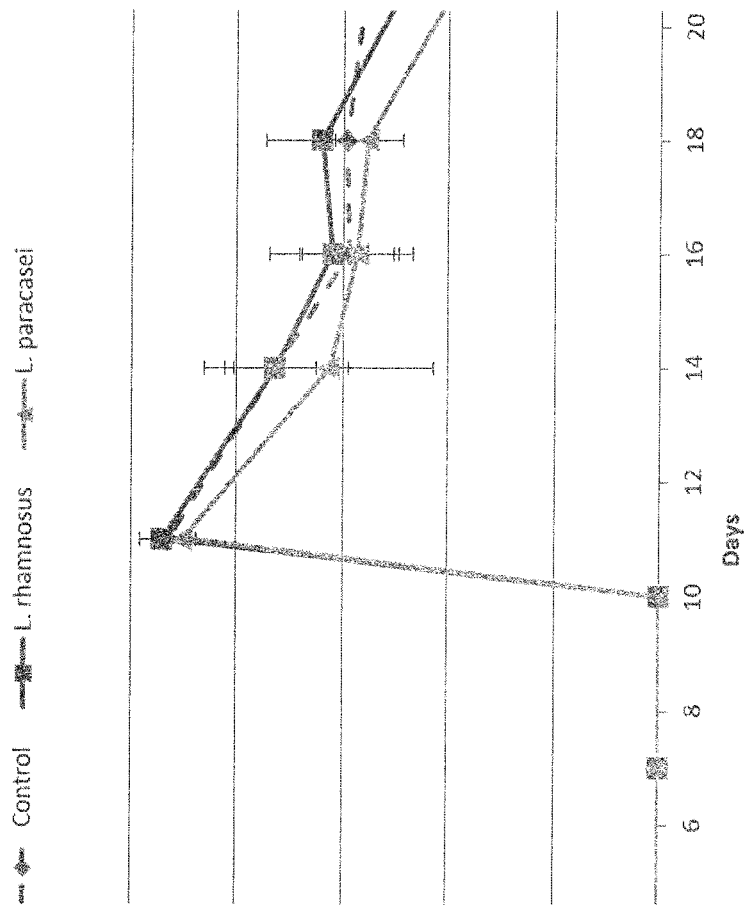
Figure 2:
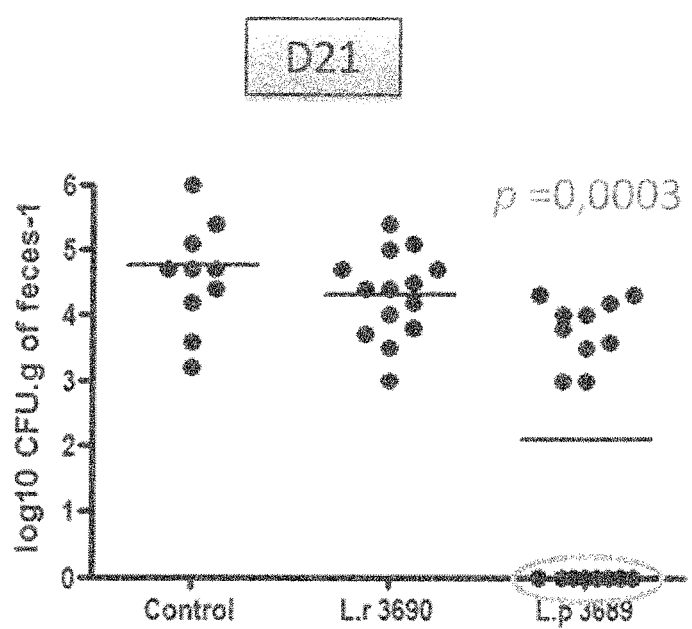
Figure 3A:
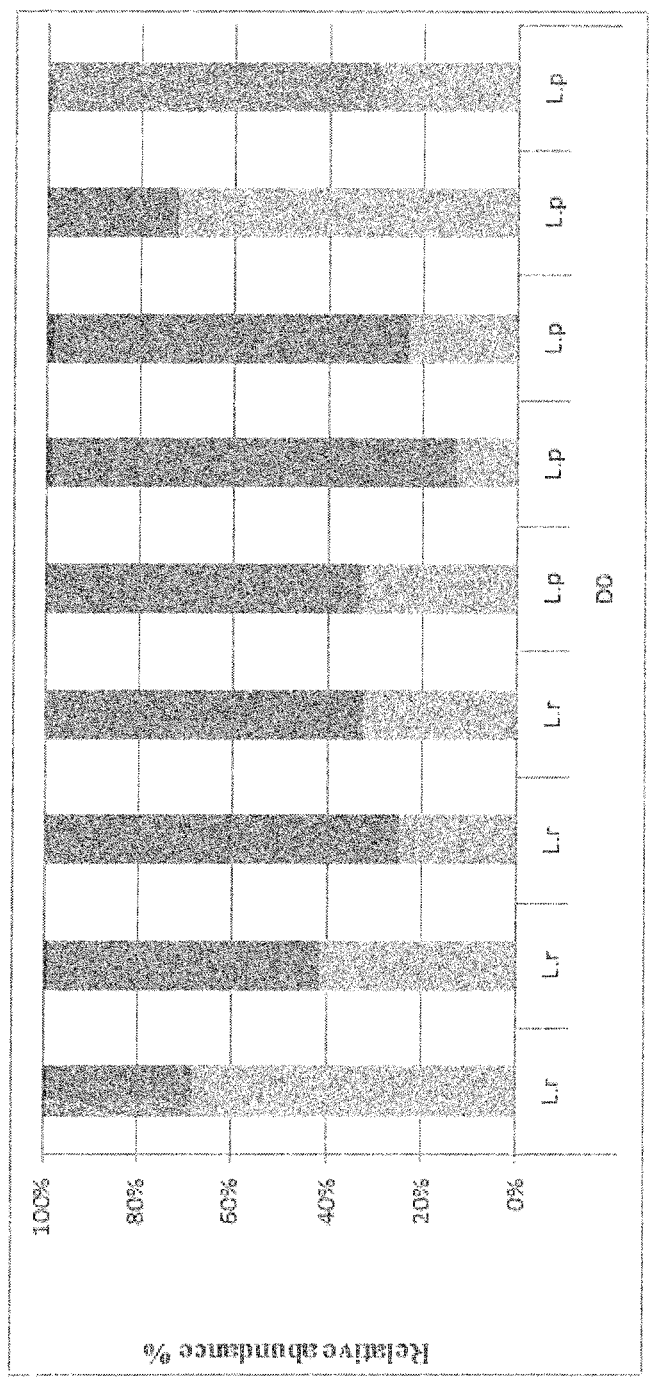
FIG. 3A) and Day 21 (sacrifice.
Figure 3B:
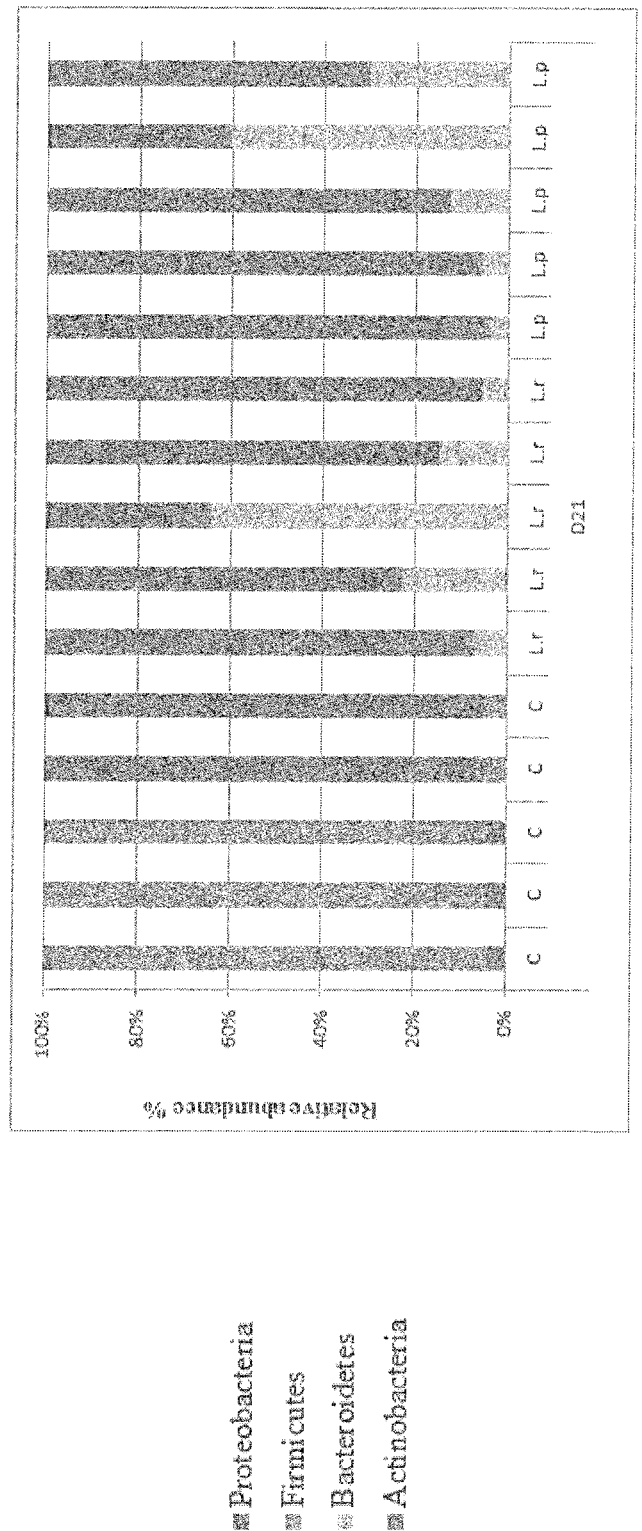
FIG. 3B) in mice fed with a daily dose of 0.1 ml of 0.9% saline solution (control "C") or fed by $10^9$ CFU of a probiotic strain (*L. rhamnosus* "L.r" or *L. paracasei* "L.p") in 0.1 ml of 0.9% saline solution by orogastric inoculation.

Taken together, these results show that administration of *L. paracasei* CNCM I-3689 significantly decreases pathogenic *E. faecalis* persistence in the gut. Given that reduction of intestinal colonization or carriage after antibiotic treatment could limit the risks of VRE infections and dissemination, *L. paracasei* CNCM I-3689 is a promising candidate to promote VRE clearance. *L. paracasei* CNCM I-3689 could be part of a non-antibiotic strategy to promote intestinal clearance of opportunistic pathogens after antibiotic dysbiosis. To profile the effects of clindamycin treatment+ VRE inoculation, and *L. paracasei* CNCM I-3689 on microbiota structure, 454 pyrosequencing of bacterial 16S rRNA gene V3-V5 variable regions was performed on fecal samples collected from mice at D0 (baseline), and D21 ("restoration"). Microbiota analysis from fecal samples collected at D0 and D21 showed that clindamycin treatment resulted in a drastic change in microbiota composition, with a predominance of Firmicutes and to a minor extent Proteobacteria in control samples. In contrast some restoration of Bacteroidetes is observed in the *L. paracasei* group (FIG. 2), and also in the *L. rhamnosus* group.

The invention claimed is:

1. A method to treat an infection caused by a vancomycin-resistant *Enterococcus faecalis* in the intestinal microbiota of a subject having a dysbiosis caused by or subsequent to antibiotic treatment of said subject, comprising administering *Lactobacillus paracasei* subspecies *paracasei* strain CNCM I-3689 to said subject.

2. The method according to claim 1, wherein said *Enterococcus faecalis* are further resistant to antibiotics selected from penicillins, cephalosporins, fluoroquinolones, aminoglycosides, and glycopeptides.

3. The method according to claim 1, wherein said *Enterococcus faecalis* are part of a High-Risk Enterococcal Clonal Complex.

4. The method according to claim 1, wherein said *Lactobacillus paracasei* is in an orally administrable composition.

5. The method according to claim 4, wherein said composition is a fermented dairy product.

6. The method according to claim 1, wherein said dysbiosis is characterized by an increase in *Firmicutes*.

* * * * *